United States Patent [19]

Kuusi

[11] Patent Number: 4,698,832
[45] Date of Patent: * Oct. 6, 1987

[54] PROCEDURE AND MEANS FOR MEASURING WITH THE AID OF A RADIO-ISOTOPE SOURCE THE DISTRIBUTION OF FILLERS IN A WEB

[75] Inventor: Juhani Kuusi, Helsinki, Finland

[73] Assignee: Robotest Oy, Finland

[*] Notice: The portion of the term of this patent subsequent to Sep. 22, 2004 has been disclaimed.

[21] Appl. No.: 638,487

[22] PCT Filed: Nov. 30, 1983

[86] PCT No.: PCT/FI83/00075
§ 371 Date: Jul. 30, 1984
§ 102(e) Date: Jul. 30, 1984

[87] PCT Pub. No.: WO84/02190
PCT Pub. Date: Jun. 7, 1984

[30] Foreign Application Priority Data
Dec. 1, 1982 [FI] Finland .................................. 824141

[51] Int. Cl.[4] ..................... G01N 23/223; G01N 33/34
[52] U.S. Cl. ........................................ 378/46; 378/45; 378/50; 378/53; 378/90
[58] Field of Search ....................... 378/45, 46, 48, 50, 378/53, 90

[56] References Cited

U.S. PATENT DOCUMENTS

| | | | |
|---|---|---|---|
| 3,102,952 | 9/1963 | Hendee et al. | 378/45 |
| 3,530,296 | 9/1970 | Lehtinin et al. | 378/45 |
| 3,904,876 | 9/1975 | Arendt | 378/53 |
| 3,914,607 | 10/1975 | Cho et al. | 250/308 |
| 4,081,676 | 3/1978 | Buchnea | 378/46 |
| 4,147,931 | 4/1979 | Puumalainen | 378/50 |
| 4,350,889 | 9/1982 | Lisnyansky | 378/46 |

FOREIGN PATENT DOCUMENTS

| | | |
|---|---|---|
| 1773085 | 3/1972 | Fed. Rep. of Germany . |
| 2727505 | 1/1979 | Fed. Rep. of Germany ........ 378/45 |
| 2946567 | 6/1980 | Fed. Rep. of Germany . |
| 3219962 | 12/1982 | Fed. Rep. of Germany . |

OTHER PUBLICATIONS

"Determination of Content and Distribution of Filler . . .", J. Kuusi, Paperi Puu 52, No. 4a, p. 145-151, 154-158 (Apr. 1970).
English Abstract from Paperchem, Access No. 50-06512, Karton No. 3, 8(1979), "Monitoring Apparatus for Determining . . . "
English Abstract from Paperchem, Access No. 46-03646, Prom No. 17: 1974, pp. 123-126, "Use of X-rays for Determining . . . "

Primary Examiner—Carolyn E. Fields
Attorney, Agent, or Firm—Steinberg & Raskin

[57] ABSTRACT

A procedure and means for non-destructively measuring the distribution of the filler and/or coating materials in the thickness direction of paper or cardboard. Radiation from a radio-isotope source is used to excite in the material component its characteristic X-ray radiation, the intensity of this radiation being observed. Measurements are made on both sides of the paper and the contents of other filler components are also determined by X-ray absorption in order to eliminate the effects of these components disturbing the distribution measurement. The base weight of the paper is measured e.g. by beta radiation absorption. Measurements are made both by measuring the characteristic radiation of the material components excited in the paper with different radiation sources and with the aid of absorption measurements of radiation directly from the source or produced with its aid in transformation targets, thus eliminating the effects of these components.

19 Claims, 12 Drawing Figures

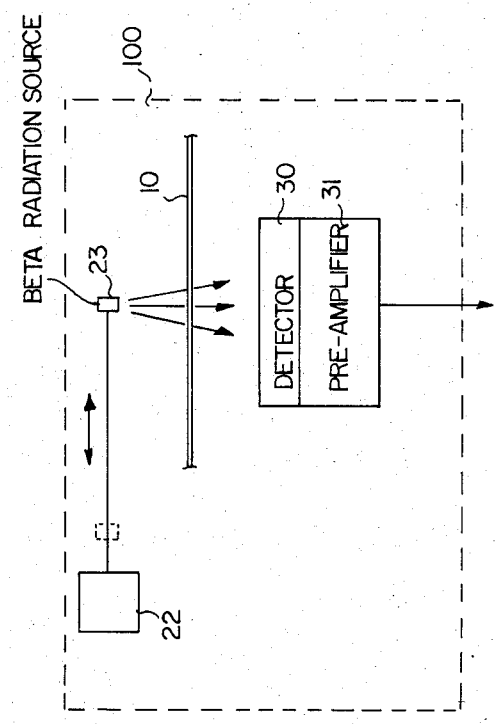

PROCEDURE AND MEANS FOR MEASURING WITH THE AID OF A RADIO-ISOTOPE SOURCE THE DISTRIBUTION OF FILLERS IN A WEB

BACKGROUND OF THE INVENTION

The present invention concerns a method for measuring the distribution in the thickness direction of filler and/or coating materials of paper, cardboard or the equivalent, and the contents of said materials without destroying the sample. In the method or procedure of the invention, the radiation emitted by an x-ray source is used to excite in the material component under examination of the object under measurement its characteristic x-ray radiation and the intensity of this radiation is observed. In procedure, measurements are carried out on both sides of the specimen under examination. In addition, the contents of other filler components are determined by x-ray radiation absorption measurements in order to eliminate the effects of such components interfering with the distribution measurement, and the base weight of the paper is determined by beta radiation absorption measurement, or by another equivalent procedure.

Furthermore, the present invention concerns apparatus for applying the method and novel uses of the procedure and the apparatus.

When paper and paper machines are discussed in the following, reference is generally made both to paper and cardboard, and respectively both to paper and cardboard machines.

Fillers, which as a rule are mineral substances, are incorporated in the paper primarily for their effect of improving the printing technological properties. Fillers are most commonly used for printing papers. The filler addition improves the opacity, lightness, printer's ink absorption and surface smoothness of the paper.

The fillers influence in a particularly advantageous manner the quality of paper to be glazed.

It is known in the art to add filler material in two ways, either by mass filling or by coating. In the mass filling method or procedure, the filler material is added in the form of suspension to the pulp sludge before the arrival of the sludge on the paper machine, whereby the filler material is admixed with the entire fiber material in the finished paper. In the coating procedure, a suitable glue substance is admixed with the filler material in the aqueous phase, such as starch or casein, whereafter the surface of the paper is brushed with this mixture in a continuous process.

The filler materials in paper tend to be non-uniformly distributed in the thickness direction of the paper, causing one-sidedness of the paper. The one-sidedness of paper manufactured on Fourdrinier machines is due to the fact that the fillers are washed out together with the water that is drained, from the lower part of the pulp web into the drainage water, whereby they become enriched in the upper part of the web. As is known in the art, efforts have been made to reduce the problems of one-sidedness, not only by additives improving the retention, but also by gentle dewatering at the initial draining phase, which requires a longer dewatering time and therefore implies lengthening the wire section or reducing the speed of the paper machine.

In machines with a planar wire, the difficulties with the fines and filler distribution manifest themselves when papers for offset printing are manufactured. A high filler and fines content on the top surface of the paper causes dusting, which is a serious detriment in the offset process. In contrast, papers manufactured on a twin wire machine are considered well appropriate for offset printing. This is due to the symmetrical shape of the fines distribution and to equal leaching of both surfaces of the web due to two-sided dewatering. It is in fact generally held that due to more uniform fines distribution, the printing by offset on paper manufactured on a twin wire machine is more successful than that on paper manufactured on a Fourdrinier machine. Offset printability has indeed increased in significance because offset printing is increasingly replacing the letterpress printing procedure.

On the other hand, the filler content of the surfaces of the paper web cannot always be brought to a desired level with a twin wire former. Even when planar wires are used only the top side of the web (the side facing away from the wire) is satisfactory as to its filler content. The low filler content of the web surface is particularly problematic in so-called SC gravure papers. Attempts may be made to increase the filler content of the paper surfaces by increasing the filler content of the pulp in the headbox, but even with this expedient, a satisfactory condition is not achieved because of the above-mentioned poor retention characteristic of the filler and of its enriching in the inner parts of the paper. In addition, when the filler content in the headbox has to be increased, the consistency in the headbox is likely to become excessive so that it impairs the formation of the paper.

Modern high-speed printing presses impose particularly high requirements on the printing paper. These requirements are based on trouble-free operation of fast printing presses and on the appearance of the printing. The imprint is considerably influenced by the symmetry between the sides of the paper and the quality of the surfaces of the paper, which is naturally also influenced by the distribution of the fillers. Heretofore no methods or procedures and apparatus have been in use with which the filler distribution could have been measured even on line either in the paper machine, in the printing press or in the paper coating means.

It is known in the art, as described in Finnish Pat. No. 40587, inventors Juhani Kuusi and Antti Lehtinen, applicant Valmet Oy, to excite the characteristic x-ray radiation of the filler material by radiations such as alpha, beta, gamma or x-ray radiation, penetrating to various depths in the paper, and in this ways to gain information on the vertical distribution of the filler. The procedure has been described in greater detail in a paper by J. Kuusi, entitled "Determination of Content and Distribution of Filler and Coating Materials in Paper Using Radioisotope X-Ray Spectrometry", Paper and Timber No. 4A 1970. As was observed in the paper, variations in relation to each other of the filler contents cause certain effects of which the quantitative elimination by the procedures described in the paper is impossible. This has impeded the introduction, practice of such procedures.

The state of the art regarding filler measurements is illustrated in general by a publication of April, 1982 by Buchnes A. McNelles L. A. and Hewitt J. S., entitled "The Application of X-Ray Absorption and Fluorescence Analysis to the Measurement of Paper Additives", Int. J. Appl. Radiat. Isot. Vol. 33, pp. 285 to 292 (1982), where a fluorescence and absorption technique is used for determining the total contents of different fillers, based on the assumption that the fillers are uniformly distributed in the thickness direction of the paper. In practice, this is hardly ever the case. It is thus understood that in this application, and the references cited therein and in its author's patent for "On-Line System for Monitoring Sheet Material Additives", U.S. Pat. No. 4,081,676, March, 1978, no endeavors whatsoever were made to determine the important thickness-direction distribution, nor has it even been taken into account as a potential source of error in determination of the total filler content. It should be noted, however, that in the instances described in the paper, the influence of said source of error is minimal.

Procedures or methods capable of determining the filler distribution and the total filler content directly in the paper machine are not in use at all.

SUMMARY OF THE INVENTION

The principal object of the invention is to provide a new method or procedure and apparatus suited, in addition to laboratory measurements for the measurement of filler distribution, which method and apparatus make possible the control and adjustment of the manufacturing process in a paper machine on the basis of filler distribution measurements.

An object of the invention is to provide a method and apparatus for determining the thickness-direction filler distribution in the paper and the total filler contents either in the laboratory or directly in a paper machine, on line.

Another object of the invention is to provide a procedure and apparatus for determining the thickness-direction filler distribution in the paper and the total filler contents when the contents of different filler components, such as, for example, $CaCO_3$, $TiO_2$, kaolin, talc or equivalent, are variable.

Still another object of the invention is to provide an opportunity not only for immediate product quality control directly in the machine, on line, but also an entirely new possibility of controlling the paper manufacturing process, the significance of which is emphasized when efforts are made to manufacture printing paper meeting ever greater quality requirements at lowest material costs. Yet another object of the invention is to achieve, measure and control the distribution, which provides an opportunity to develop the paper machine construction and the total control system of paper machines.

Another object of the invention is to provide a method which is suitable for quality control of the paper fed into fast modern printing presses, and possibly for the control and/or adjustment of the operation of printing presses.

To achieve the aims presented in the foregoing and those which will hereinafter become apparent in the method of the invention, the distributions of fillers and equivalent are determined by combined processing of the two following sets of measurements.

1. Absorption measurements for determining the contents of different filler components with radiation obtained directly from the source or produced with its aid in appropriate transformation targets; as many measurements as there are filler components to be considered separate ones.

2. Measurements of the characteristic radiation of the material components excited in the paper by different sources of radiation.

In the apparatus of the invention a measuring head comprising radiation sources and transfer mechanisms therefor, a radiation transformation plate or plates and a transfer mechanism therefor, and a radiation detector and a pre-amplifier. The measuring head is connected to a measuring device having a power source, an amplifier and a counter, processor and display unit.

A second embodiment of the apparatus of the invention comprises a measuring head with an x-ray source emitting radiation varying in energy during the measuring cycle in a known manner, and radiation detectors and pre-amplifiers. The measuring head is connected to a measuring apparatus comprising power sources, amplifiers and a multi-channel counter, processor and display unit using a time axis.

The method or procedure and apparatus hereinbefore described are used, as taught in the invention, for example in a paper machine, in on-line measurement for measuring the filler distribution in the thickness direction and the total filler content of paper. In addition, the obtained measurement may be used as feedback signals in the control system of the paper machine, in the control of the filler distribution, and/or of the total filler content of various filler materials. An advantageous application of the invention is in measurement, and possibly in the control, of the coating material content and/or coating material distribution in paper or cardboard that is either being coated in an on-line process, or has been tested in a separate coating apparatus, in particular of its one-sidedness.

One potential application of the invention is the quality control of the paper being fed into a printing press and/or governing, and possibly controlling, the operation of the printing press.

As has in part become apparent from the foregoing, the inventive idea is that the intensity of the characteristic x-ray radiation of the filler component excited with different radiation sources, and possibly with different angles of incidence of the exciting radiation, is measured on both sides of the paper. This intensity provides information about the shape of the distribution. In addition, in this x-ray fluorescence measurement it is possible to determine, the intensity of the exciting radiation scattered back from the paper and which correlates, for example with the base weight of the paper. What is significant from the point of view of practical applications is that the contents of various filler components are measured by x-ray absorption measurements. These measurements make use of the primary radiation emitted by a radiation source and a radiation with desired absorption properties which has been derived from this source, or from a source placed on the other side of the paper, with the aid of appropriate transformation targets. The auxiliary quantity is the absorption measurement signal of beta radiation used as routine in measurements on paper for determinations of base weight in $g/m^2$ (fibers plus filler). Based on the results of the absorption measurements, it is possible by calculation to eliminate the effects of the variation of the different filler components' contents on the fluorescence measurements, and in this manner to determine the filler distribution and the contents of different filler components.

In the laboratory, the invention affords an opportunity for rapid quality control of the paper, and thereby for the control of the manufacturing parameters with a given lead time. Particularly the filler distribution close to the surface layers of the paper has considerable significance concerning the printability of the paper. Furthermore, a distribution of proper shape provides an opportunity to use filler in abundance, thereby lowering the total material costs. The procedures or methods presently used in laboratories, such as dividing the paper into different layers by a tearing tape, incineration of layers and ash determination, are slower by one order of magnitude and more inaccurate than the method of the invention.

BRIEF DESCRIPTION OF THE DRAWINGS

For a fuller understanding of the invention, reference is had to the following description, taken in connection with the accompanying drawings, in which.

DESCRIPTION OF THE PREFERRED EMBODIMENTS

Figure 1:
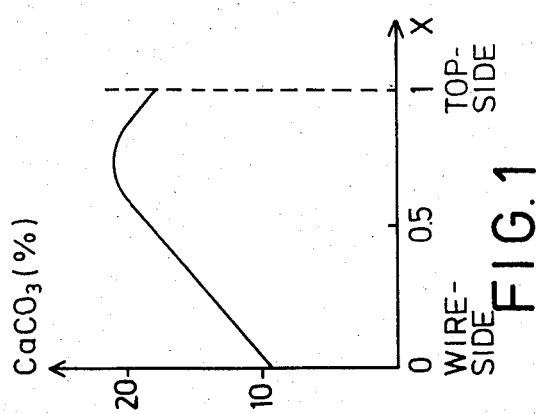
FIG. 1 is a graphical representation of a typical filler distribution in paper manufactured on a Fourdrinier machine.

A typical filler distribution of paper in its thickness direction x is shown in FIG. 1. The filler is least in quantity on the wire side. In this instance, the maximum is reached slightly above the center-point of the paper, marked 0.5 on the horizontal axis. The filler content decreases towards the top surface (x=1).

The attenuation or extinction of x-ray, gamma and beta radiation in matter can generally be expressed by the expotential formula:

$$I = I_o e^{\mu m},$$

where $I$ (1/s) is the intensity of the radiation that has gone through a mass course m (g/cm$^2$), $I_o$ (1/s) is the original intensity of the radiation and $\mu$ (cm$^2$/g) is the absorption coefficient representing the extinction or attenuation capacity of the material.

Figure 2:
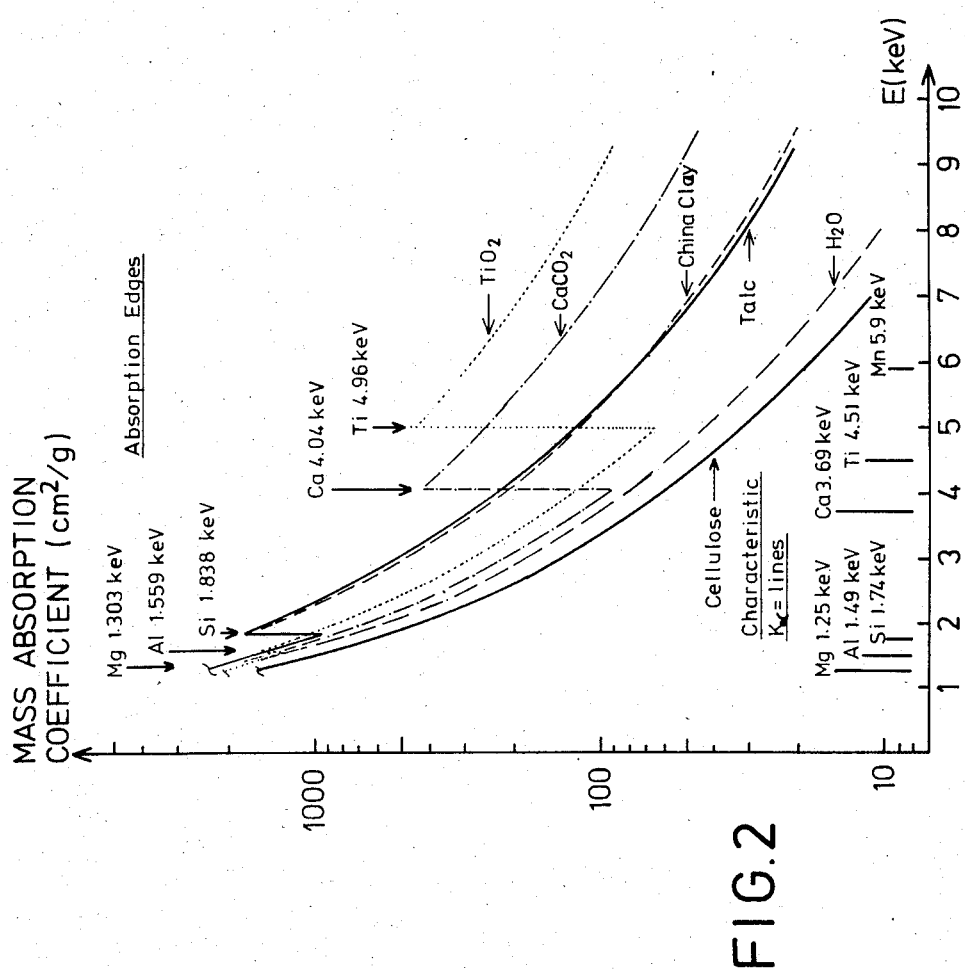
FIG. 2 is a graphical representation of mass absorption coefficients of some mineral filler and coating materials of paper and of water, of cellulose for low energy x-ray raidation.

The absorption coefficients for low energy (1 to 10 keV) x-ray and gamma radiation of material which are important in view of filler measurements are set forth in FIG. 2, plotted over energy. Both are the same type of electromagnetic radiation. In FIG. 2, the abscissa represents the energy (in keV) and the ordinate represents the absorption coefficient $\mu$ (in cm$^2$/g). With the exception of a few discontinuous irregularities, the absorption coefficient and therefore also the attenuation in the material, decreases with decreasing energy. However, some of the discontinuous jumps seen in FIG. 2 are of central importance in the embodiments of the invention. If the graph of the absorption coefficient of calcium carbonate (CaCO$_3$) is scrutinized, we find that it depends smoothly throughout the range from 1 to 4 keV, until, at 4.04 keV energy, its value discontinuously increases to be tenfold and thereafter once more decreases smoothly with increasing energy of the radiation. The physical cause underlying this jump is that in the range under consideration, x-ray and gamma radiation are attenuated in the material in the manner that the energy of the radiation quanta transfers totally to electrons in the atoms. Such electrons, by virtue of the energy imparted to them, are flung out from the atom, leaving behind a vacancy in the electron shroud. The energy of the x-ray or gamma quantum has to be higher than the binding energy holding the respective electron to its atom. When the energy of the radiation is lower than the 4.04 keV corresponding to the jump in the graph for CaCO$_3$, the radiation is not able to detach the electrons of its inner shell (the K shell), which are the electrons most strongly bound to the atom from the calcium atom. When the energy of the incident radiation surpasses this limit, its quanta can become absorbed in the substance by detaching electrons from the inner shell, and this exactly gives rise to the discontinuous increment of the absorption coefficient. The higher the atomic number of a substance, in practice usually the heavier it is, the higher is the energy at which is found this K absorption limit, that is the absorption limit corresponding to the K shell.

Thus, it is hown in FIG. 2 that the K absorption limit, due to titanium, of titanium dioxide (TiO$_2$) is located at an energy of 4.96 keV. In talc and kaolin, the element with the highest atomic number is silicon (Si), and therefore the absorption coefficient decreases steadily after the absorption limit of silicon at 1.8 keV with increasing energy of the radiation.

It is thus understood that when radiation having an energy higher that the K absorption limit of calcium is directed on a substance, for example calcium, vacancies will form on the inner electron shells of the atoms. When these are filled by electrons falling from outer shells, the substance emits its characteristic K x-ray radiation, the energy of which because of recoil losses is slightly lower than the energy of the K absorption limit. The strongest line of the calcium K has energy 3.69 keV, which has also been indicated on the energy axis in FIG. 1.

The characteristic x-ray radiation of each element produced through absorption is utilized in a manner known in the art in x-ray fluorescence analysis for determining the chemical composition of the specimens being analyzed. In the invention, the absorption is utilized towards determining the filler content of the paper's different layers and thus towards determining the filler distribution. In order that the determination of the distribution could be made sufficiently free of error from the viewpoint of the practical applications, the total contents of the different filler components in the paper must be known. This is determined in the invention, by absorption measurements.

If, in the absorption measurements, the attenuation or extinction caused by paper containing filler is measured with two radiation energies which are as close as possible to the absorption limit of a given component in the manner that one energy is above and the other below the limit, the difference in the attenuation or extinction caused by the paper will furnish information about the content of such filler component. If the paper contains kaolin, talc, calcium carbonate and titanium oxide as fillers, the difference in the attenuation or extinction of the 5.9 keV line emitted by the $^{55}$Fe radiation source and of the K line of titanium (4.51 keV) will furnish information primarily about the titanium dioxide content (FIG. 2), the difference in the attenuaion extinction of the difference of 4.51 keV (Ti K) and 3.69 keV (Ca K) radiations will furnish information about the CaCO$_3$ content, and the absolute attenuation or extinction of the 3.69 keV radiation, primarily about the combined content of talc and kaolin, these latter components having absorption components which at the last-mentioned point are clearly higher than the absorption coefficients of any other components of the paper, as shown in FIG. 2.

In order to determine the contents of various filler components of paper, it is necessary to know the base weight of the whole paper, that is, its mass per unit area in g/m$^2$. This is found by measuring the attenuation extinction in the paper of beta radiation for example from an $^{85}$Kr source. This is because the different components of paper cause equal attenaution or extinction of beta radiation that is, of electrons thrown out by nuclei. The use of beta radiation for determining the base weight of paper is known in the art of paper technology and is completely routine in its nature.

Figure 3:
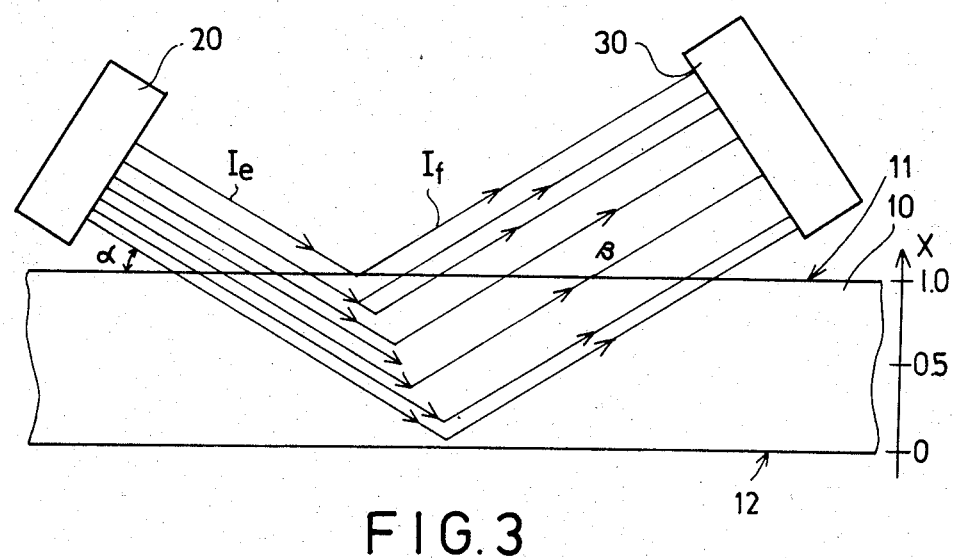
FIG. 3 is a schematic diagram illustrating the main principle of the fluorescence measurement of the invention.

The fluorescence measurement used for the actual determination of the filler distribution is described more specifically with reference to FIG. 3, in connection with which it is assumed that the base weight of the paper specimen 10 is 100 g/m$^2$ and that it contains, as uniformly distributed filler 25% calcium carbonate. As shown in FIG. 3, the exciting radiation $I_e$, in the case under consideration, 5.9 keV radiation from the $^{55}$Fe source 20, impinges on the paper specimen 10 at an angle of incidence $\alpha$ and excites in the specimen 10 the characteristic radiation of calcium, of 3.69 keV. The detector 30 measuring the radiation $I_f$ observes the radiation departing at an angle $\beta$ from the surface 11 of the specimen 10. Since the exciting radiation $I_e$ is attenuated as it proceeds in the paper specimen 10, it excites calcium radiation more efficiently in the adjacent top surface 11, which is closer to the source 20, than in the lower, or back, surface 12. Since the excited characteristic radiation of calcium is also attenuated in the specimen 10 to a given extent, the radiation excited adjacent the top surface 11 has easier access to the detector 30.

Figure 4A:
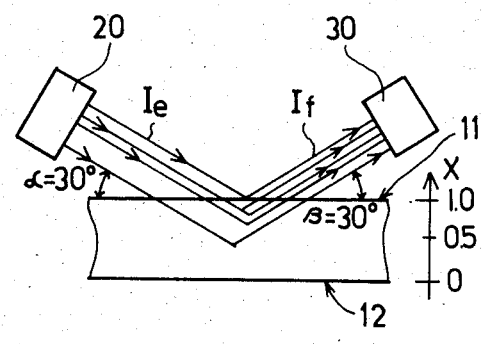
FIGS. 4A and 4B are schematic diagrams presenting the principle of the fluorescence measurement of the invention with two different angles of incidence of the exciting radiation and angles of departure of the excited radiation.
Figure 4B:
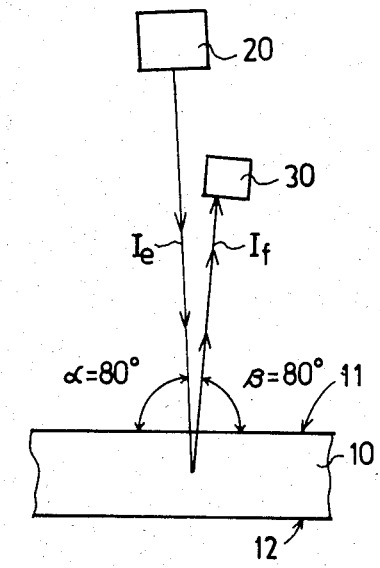

Both of the just mentioned act in the direction that the greater part of the radiation detected by the detector 30, in the case of homogeneous filler distribution, comes from the top layers of the specimen 10, and therefore the topmost layers of the paper will be emphasized in the information thus obtained. The smaller the angles of incidence and departure $\alpha$ and $\beta$ of the radiation, the greater are the differences in path length between the top surface 11 and the lower surface 12, and the greater is the stress placed on said top 11 in the information gained by the detector 30. In this manner, it is possible by varying the angles of incidence and departure $\alpha$ and $\beta$, to change the relative weight factors of different layers in the information that is measured. This is demonstrated by FIGS. 4A and 4B and by the following Table 1.

TABLE 1

| | | | |
|---|---|---|---|
| Angle of incidence of the radiation ($\alpha$) | | 80° | 30° |
| Angle of departure of the radiation ($\beta$) | | 80° | 30° |
| | Depth | Intensity | Intensity |
| Relative intensity of information from different depths in the paper | 0.05 | 0.93 | 0.86 |
| | 0.5 | 0.47 | 0.22 |
| | 0.95 | 0.23 | 0.06 |

Table 1 shows the relative intensity of the information received in fluorescence measurements (CaK line; $^{55}$Fe source) at various depths in the specimen when two different pairs of angles of incidence and of departure $\alpha$, $\beta$ of the radiation are used. The base weight of the paper is 100 g/m$^2$ and its CaCO$_3$ content is 25%, assumed in this calculation example to be uniformly distributed in the vertical direction. On the depth scale, the surface is denoted by coordinate 0 and the back side of the paper is denoted by the value 1, making the coordinate of the center 0.5.

The intensity values calculated in Table 1 reveal that the information is strongly weighted in favor of the top side, in other words, emphasizing the side at which the measurement is performed. This effect is considerably strengthened upon changing the angles of incidence and departure of 80° in FIG. 4B to the angles $\alpha$, $\beta$ of 30° in FIG. 4A. This is seen when, for instance, the values of the intensities obtained from the center of the paper (0.5) are mutually compared (0.47 and 0.22).

Another manner of varying the relative weighting of the different layers is to use sources with different energies for excitation radiation. If, in the case just considered, the $^{55}$Fe source (5.0 keV) is replaced with a $^{238}$Pu source, of which the strongest radiation components have an energy 12–17 keV, the attenuation of this in the paper is so minimal that excitation will occur more or less uniformly throughout the thickness dimension of the specimen 10. For the excited radiation $I_f$, of course, the attenuation extinction effects are the same, independent of what radiation has affected the excitation.

If the distribution of a given filler component in the thickness direction of the specimen 10 is not uniform but, for example, as shown in FIG. 1, the intensities of the characteristic radiation of calcium measured on different sides of the paper are unequal and their difference reflects the one-sidedness of the distribution. A paper having a distribution substantially as in FIG. 1, with a base weight of 160 g/m$^2$ and a calcium carbonate content of about 20%, yielded with a $^{55}$Fe source and with angles $\alpha$, $\beta$ of incidence and departure, averaging 80°, the ratio 470/410 between different sides (top side/-wire or lower side) was found. When the angles of incidence and departure were reduced, the ratio increased, as could be expected. An effect in the same direction was achieved using a $^3$H/Tl source, which emits softer (4.5 keV) radiation than the radiation of 5.9 keV of the $^{55}$Fe source.

The determination of the filler distribution on the basis of the results of measurement will now be considered.

The basic distribution as in FIG. 1, can be mathematically represented by a polynomial $y=ax^2+bx+c$, where y refers to filler content (ordinate) and x to the coordinate in the vertical direction of the paper (abscissa). The coefficients a, b and c are found by fitting to a reference distribution. The intensities of the characteristic radiation of calcium are determined from both sides of a paper with reference distribution to serve as reference values, as is the x-ray absorption of the paper with a suitable source for example a $^{55}$Fe 5.9 keV, and the beta absorption such as for example $^{85}$Kr source.

Then when the equivalent quantities are measured from an unknown specimen belonging to the same paper brand, the differences between them and of the quantities measured from the reference paper will yield the filler distribution of the paper sample being measured, by mathematical methods, utilizing the known absorption coefficients of the different components. In the vicinity of the reference distribution, a measurement carried out with merely one pair of angles $\alpha$, $\beta$, or with one source provides a rather reliable estimate of the distribution. The reliability and accuracy can be increased by varying the angles of incidence and of departure $\alpha$, $\beta$, by using several sources 20 emitting energy $I_e$ with different energies. This naturally causes the mathematical processing to be more complicated.

In a case which was studied, the reference polynomial representing the filler distribution was found to be $y=-42x^2+52.1x+6.7$, the unit of y and the coefficients a, b and c being the $CaCO_3$ content in %. It follows that the $CaCO_3$ according to the reference distribution is 6.7% on the wire surface 12 (x=0) of the specimen 10, and 16.8% on the top surface 11 (x=1).

After the measurement results for the intensity I of the characteristic radiation of calcium where $I_1$ is the wire side 12 and $I_2$ is the top side 11, and the result of the x-ray absorption measurement T for the paper specimen under examination have been corrected by applying the reference graph, with the aid of the results of the beta absorption measurements to correspond to the base weight of the reference paper, the changes $\Delta a$, $\Delta b$, $\Delta c$ of the coefficients of the distribution polynomial for the paper under examination can be calculated from the system of equations calculated from the reference polynomial.

$$I_1/I_1 = 0.6113\cdot\Delta a + 1,127\cdot\Delta b + 3,344\cdot\Delta c$$

$$I_2/I_2 = 1.0403\cdot\Delta a + 1,832\cdot\Delta b + 2,781\cdot\Delta c$$

$$T/T = \tfrac{1}{3}\cdot\Delta a + \tfrac{1}{2}\cdot\Delta b + 1 - \Delta c$$

In the system of equations, $\Delta I$, $I a \Delta$ and $\Delta T$ correspond to the values of the paper specimen 10 under examination and to those measured from the reference paper.

In tests that have been carried out, the new coefficients obtained from the system of equations were found to yield distributions in agreement with the distributions determined from the same paper specimens by activation analysis close to the reference distribution. It is obvious that a more accurate approximation is attained by a greater number of measurements, but the accuracy afforded by the procedure described in the foregoing is adequate in certain supervision applications.

If in the example under consideration, kaolin, for example, is added to the filler of the paper in addition to calcium carbonate, as is frequently done intentionally or inadvertently in reused paper, etc., the situation is significantly altered in the sense of measuring technology. This is because kaolin attenuates, in fluorescence measurements, both the exciting $I_e$ and the excited $I_f$ radiation, especially the $I_f$ radiation, and as a result the variations of kaolin content affect to a certain degree the calcium carbonate measurements, even if the content and distribution of the calcium carbonate should be constant in the specimen 10. The influence of kaolin on the results is however calculable and can be eliminated with the aid of the known absorption coefficients, provided that the kaolin content in the specimen 10 is known. This leads to the requirement of measuring technology that, in connection with the measurements the contents of kaolin and other potential filler components have to be determined. This is possible by using suitably selected radiation energies in the absorption measurements, as hereinbefore described. It may be observed, in this connection, that of the commonly used fillers, talc and kaolin are materials of which the contents must be determined by the absorption technique. Fluorescence measurements do not succeed in normal conditions because in these substances the characteristic x-ray radiation, even of the heaviest element, silicon (Si), is so weak that it is excessively attenuated in the specimen 10, in the air space and in the windows of standard detectors 30. The same methods applied for $CaCO_3$, may be applied for $TiO_2$, which is occasionally used with the difference, of course, that the K line (4.51 keV) of titanium is excited and measured.

It is thus understood that in complicated cases the determination of the thickness-direction distribution of filler requires several x-ray fluorescence measurements on both sides of the specimen 10 and several absorption measurements. The intensity of the exciting radiation $I_e$ scattered back from the specimen 10, which correlates with several characteristics of the specimen paper may be used as a kind of control quantity in the measurements. In practice, when one is moving quite close to a given reference distribution, adequate accuracy is often achieved with rather few measurements.

Figure 5A:
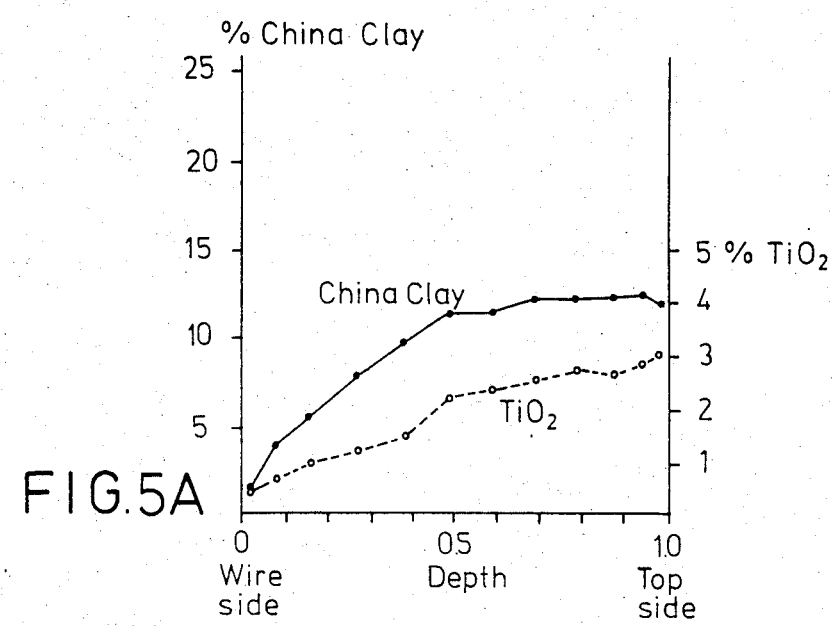
FIG. 5A is a graphical representation of the distribution of filler components prior to coating the paper.
Figure 5B:
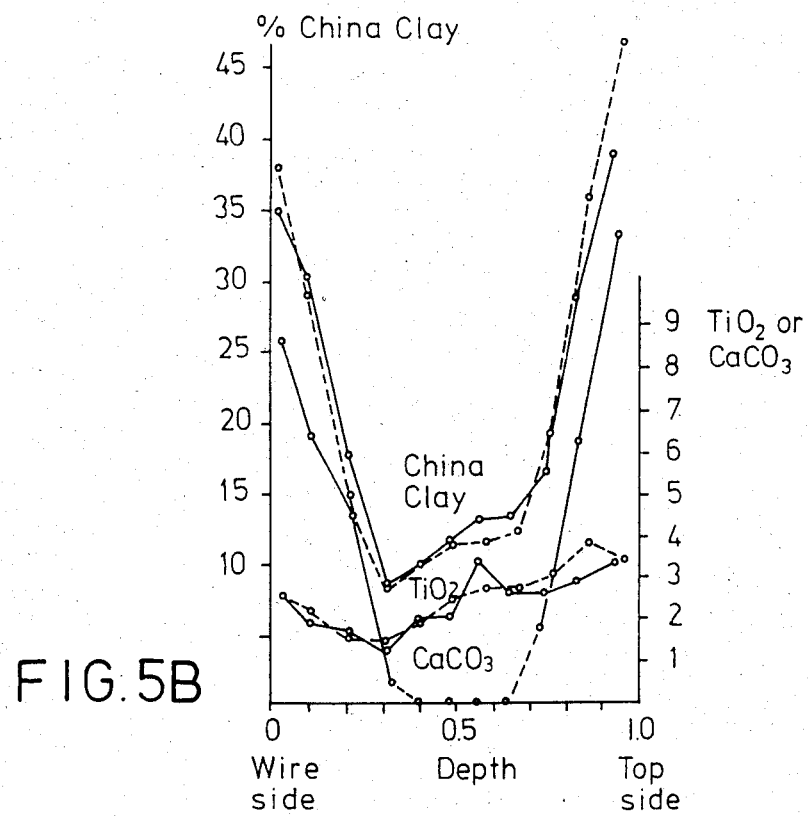
FIG. 5B is a graphical representation of the same paper after the coating process.

The printing characteristics of paper can be improved by coating the paper with the same substance that are used as fillers. In this case, the contents of mineral components in the surface layers of the paper increase greatly, as seen in FIGS. 5A and 5B. Since the method of the invention provides information about the distribution of the mineral components in the paper and, in particular, about the content in the surface layers of the paper, it is also possible to determine the amount of coating in the coating layers and the difference in coating between the different sides of the paper by the method of the invention without destroying the specimen. If the paper is already coated, the filler distribution of the uncoated bottom paper naturally cannot be elicited any longer.

The part isolated by interrupted lines in FIGS. 6A, 6B, 6C and 6D is the measuring head 100. The measuring head 100 comprises radiation sources 20 and their transporting mechanisms 22 known in themselves in the art, radiation transformation plates and their transfer mechanisms 22 (not presented in detail), a radiation detector 30 and a pre-amplifier 31. In laboratory apparatus, the measuring head 100 is, for example, an enclosed apparatus on the table, into which the paper specimen 10 to be examined is conveyed by a suitable mechanism, which transports the paper during one measuring cycle into one or several measuring positions.

Figure 7:
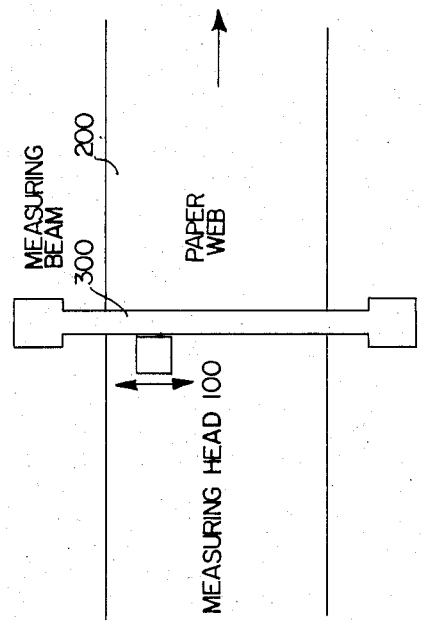
FIG. 7 is a schematic diagram of a measuring head disposed on a transverse measuring beam for reciprocating movement over the paper web.

In an in-line apparatus performing the measurements directly on the paper machine, the paper web 200 of FIG. 7 passes through the measuring head 100 mounted on a measuring beam 300. The measuring head 100 may be so constructed that it may traverse the paper web, as shown in FIG. 7.

The detector 30 consists of a proportional counter. In certain instances, in particular, in laboratory measurements, a semiconductor counter may also be used with a view to increasing the accuracy.

The measuring head 100 is connected to measuring apparatus 40 comprising a voltage source 41, an amplifier and a counter, processor and display unit 42. A control unit 43 connected to the processor governs the performing of the measuring cycle and the processing of results.

In the laboratory version of the means of the invention, the processor functions may be replaced by manual operations, and the results may, of course, be processed manually or by an external computer 50. In fact, the measuring equipment external to the measuring head 100 is standard measuring equipment, and the inventive idea proper is associated with the measuring head 100.

The extent of the equipment external to the measuring head 100 and of the computer 50 software and programs is greatly dependent upon the degree of automation and the standard of accuracy desired, and, the extent of the measuring range, that is on the number of different paper brands and the variation limits, within each brand, of the quantities which are measured.

Figure 6:
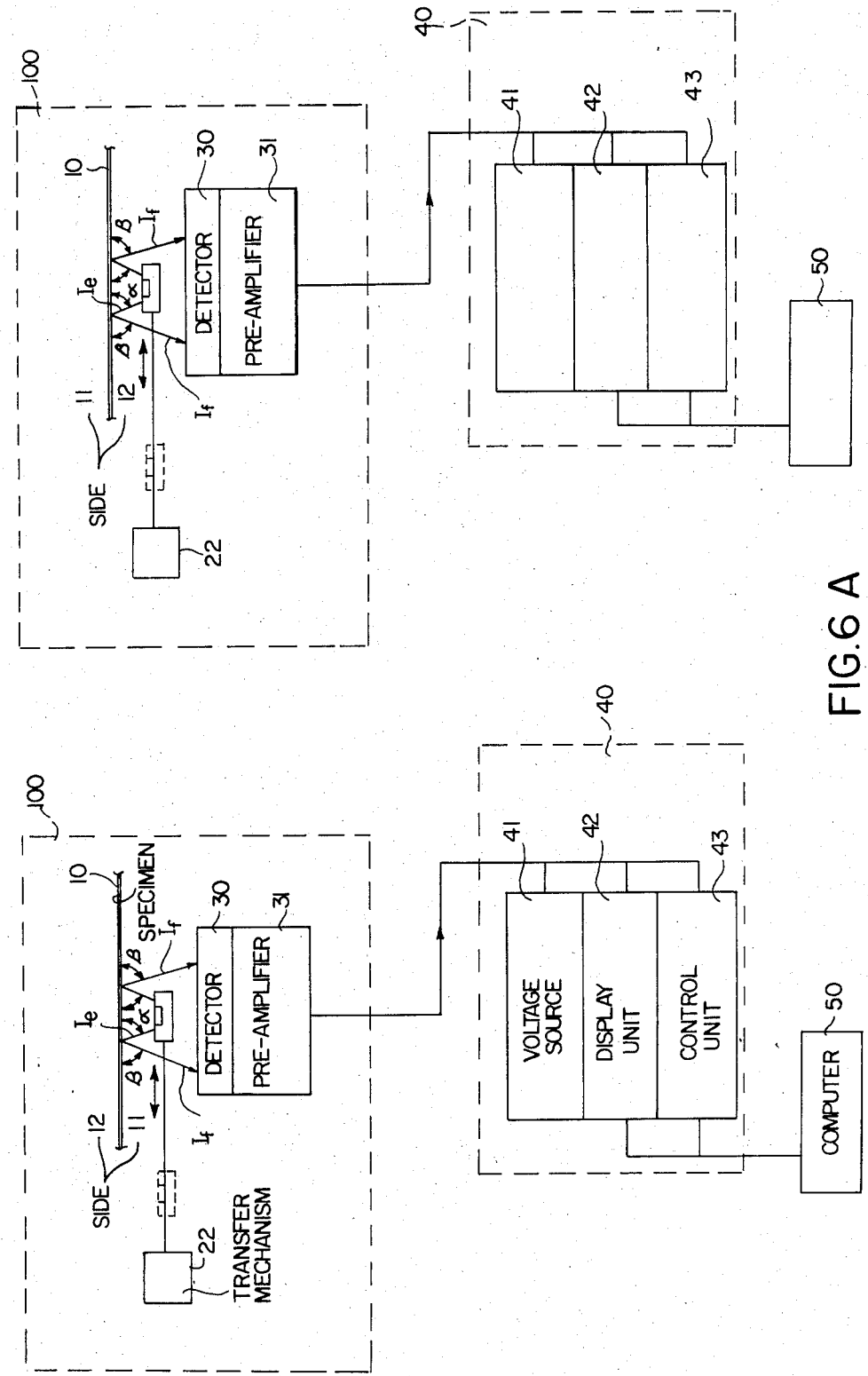
FIG. 6A is a schematic diagram of an embodiment of the apparatus of the fluorescence measuring apparatus of the invention.
FIG. 6B is a schematic diagram of a second embodiment of the apparatus of the invention for absorption measurement with x-ray radiation.
FIG. 6C is a schematic diagram of a third embodiment of the apparatus of the invention for absorption measurement with beta radiation.
FIG. 6D is a schematic diagram of a fourth embodiment of the invention alternative to FIG. 6C for absorption measurement with x-rays.

FIG. 6A illustrates the exciting of the characteristic fluorescence radiation of a filler component $CaCO_3$ or $TiO_2$ and its measuring at the other side of the paper specimen 10. The radiation emitted by the radiation source 20 excites in the specimen 10 the characteristic x-ray radiation of a given element (Ca or Ti) of a filler, part of which is directed to the detector 30 and counted. The detector 30 differentiates between the different types of radiation by their energy with such accuracy that the contribution of each radiation component can be determined by mathematical means from the measured pulse height distribution. If it is desired to make the measurement at exciting radiations $I_e$ having different energies, the source of radiation 20 may be exchanged with the aid of a suitable mechanism. If, again, it is desired to utilize different angles of incidence and departure, $\alpha, \beta$ of the radiation with reference to the surface of the paper specimen 10, it is possible to move the source 20 laterally and to use appropriate collimators or radiation beam detectors, known in the art.

FIG. 7 is a schematic diagram of a measuring head 100 mounted on a transverse measuring beam 300 in a paper machine to perform on-line measurement traversing reciprocatingly the width of the travelling paper web 200.

Since for determining the filler distribution, a fluorescence measurement has to be made at both sides of the specimen, in the laboratory version, the paper specimen 10 must be turned over, or two measuring heads 100 carrying out measurement at different sides of the specimen 10 have to be used. When measurements are carried out directly in the paper machine, the only possible alternative is the two heads.

Figure 6B:
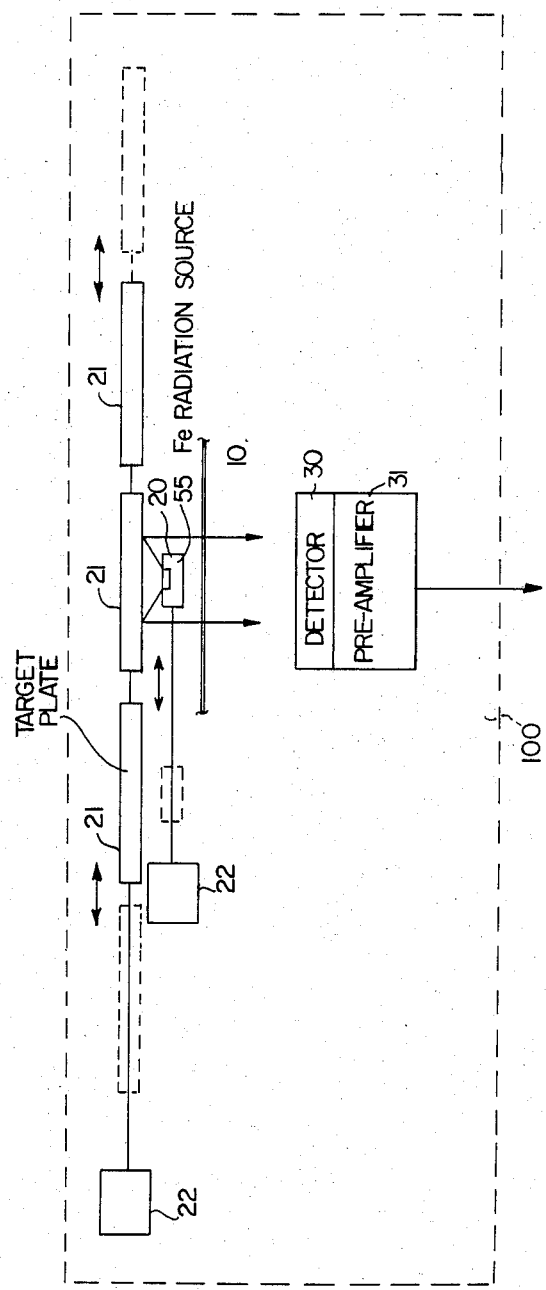
Figure 6:
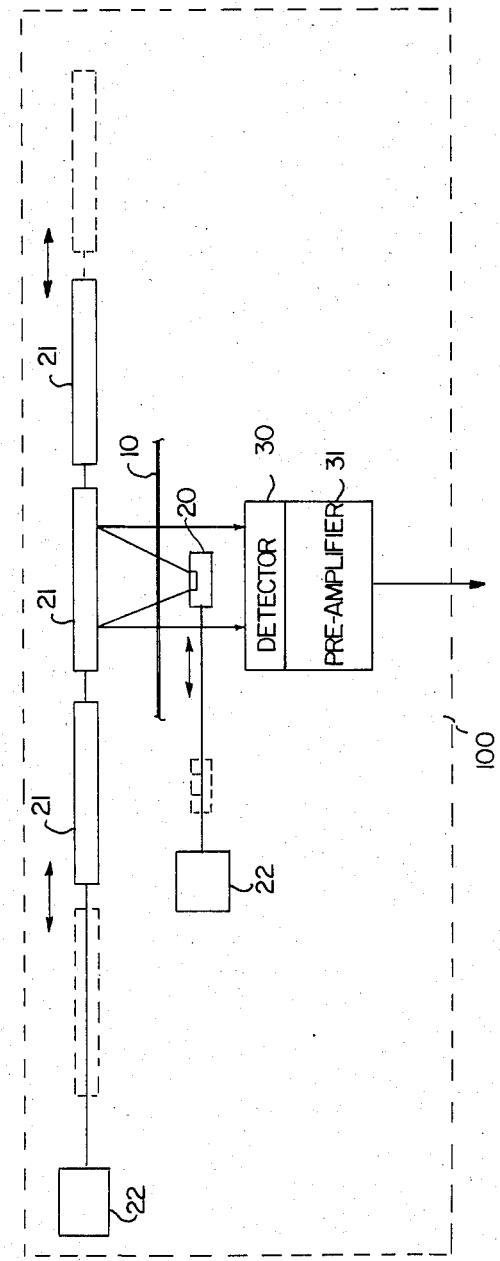

FIG. 6B presents an arrangement by which absorption measurements are carried out with x-ray radiation of different energies. The radiation from the radio isotope source 30 is either scattered by an exchangeable target plate 21 or excites therein radiation appropriate for absorption measurements, such radiation passing partly through the paper specimen 10 into the detector 30. The 5.9 keV ($^{55}$Fe), 4.51 keV (Ti K) and 3.69 keV (Ca K) radiation components which were hereinbefore required in the absorption measurement example are obtained with the aid of a $^{55}$Fe source by means of plastic or scattering, titanium or marble target plates 21. In specific instances, the absorption measurements, too, may be performed with the aid of the source used in the fluorescence measurements, as shown in FIG. 6C.

As shown in FIG. 6C, the radiation that has passed from the source 20 through the specimen 10 is scattered from the backing plate 21 or excites therein radiation appropriate for absorption measurements, which radiation partly passes through said specimen into the detector 30. In this instance, the signal of the radiation excited in the paper specimen 10 by the source 20, which signal reduces the accuracy of measurement in certain cases is admixed with the signal being measured.

FIG. 6D presents the absorption measurement, apparatus of the invention, used in routine in the papermaking industry for base weight measurements and carried out with the aid of a beta radiation source 23. This measurement provides the auxiliary quantity which is indispensable in the processing of the results of measurement in distribution measurements according to the invention.

Detailed reference distributions which are indispensable for demonstrating and proving the practical applicability of the method of the invention may be determined by neutron activation analysis of microtome sections made of paper. The technique is described in an article by Kuusi, J. and Lehtinen, A. J. entitled "Neutron Activation Analysis of Microtome Cuts in Examination of Paper for Its Filler Distribution", Pulp and Paper Magazine of Canada, 71, No. 3 (1970).

The method and apparatus hereinbefore described are suitable for use either in laboratory measurements or on-line measurements in a paper machine. In the on-line measurement use, the results obtained by the measuring apparatus may be used as feedback signals for guiding and/or controlling the papermaking process towards implementing a desired filler distribution. A possible application of the invention is the use of the method or apparatus in the measurement, and possibly even in the control, of the coating agent content and.or coating distribution either of paper or cardboard to be coated in an on-line process, or of paper treated in separate coating means, in particular of its one-sidedness. Further applications of the invention may be the quality control of paper fed into a printing press, and even the guiding control of the operation of a printing press for optimizing the printing press.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A method of measuring, without destroying the specimen, the distribution in the thickness direction of the filler and/or coating materials of paper or cardboard, and the content of said materials, wherein radiation emitted by a radio-isotope source is used to excite in the material component to be examined, of the object of measurement, its characteristic X-ray fluorescent radiation, the intensity of said characteristic radiation being observed, measurements are made on both sides of the paper or cardboard under examination, the contents of filler components are determined by X-ray absorption measurements for eliminating the effects of these components disturbing the distribution measurement, and measurement is made of the base weight of the paper or cardboard under examination, in g/m², by radiation absorption measurement, said method comprising the steps of
    making a number of X-ray absorption measurements, the number of measurements being at least equal to the number of different filler components which are to be considered separate from the point of view of X-ray absorption measurements, for determining the contents of the different filler components and the coating materials by X-ray radiation;
    making a number of measurements of the characteristic X-ray fluorescent radiation of the material components excited by a radioisotope source and
    determining the distribution of fillers and coating materials by calculative joint processing of the results from said measurements.

2. A method as claimed in claim 1, wherein radiation is obtained directly from said source.

3. A method as claimed in claim 1, wherein radiation is provided by use of a transformation target.

4. A method as claimed in claim 1, further comprising the eliminating the effects exerted on the fluorescent measurements by variations of the different filler components' contents relative to each other by calculation with the aid of the total contents of the different filler components determined by X-ray absorption measurements in a manner whereby the thickness direction distributions of the different filler components in the paper or cardboard is determinable from the fluorescence measurements.

5. A method as claimed in claim 1, wherein the distributions of different material components are measured by the use of radiation sources with different energy levels (E), each energy level (E) being selected so that it is slightly higher than the Kα absorption limit of the material component to be examined.

6. A method as claimed in claim 1, further comprising the step of determining the intensity of the radiation from said radio-isotope source scattered back from the paper or cardboard, which correlates with the base weight of the same, so as to provide an auxiliary quantity in the processing of results, in addition to X-ray fluorescence measurements.

7. A method as claimed in claim 1, wherein the contents of various filler components are measured by X-ray absorption measurements utilizing the primary radiation emitted by said radiation source and radiation with certain adsorption properties derived from said source.

8. A method as claimed in claim 1, wherein the contents of various filler components are measured by X-ray absorption measurements utilizing the primary radiation emitted by said radiation source and radiation from a source placed on the other side of said paper or cardboard via a transformation target.

9. A method as claimed in claim 1, wherein the filler material of said paper or cardboard examination is principally kaolin, talc, calcium carbonate and/or titanium oxide, said method utilizing 5.9 keV radiation emitted by a $^{55}$Fe radiation source as the primary radiation source and that of the characteristic 4.51 keV K line excited in titanium primarily in determining the titanium dioxide content, utilizing the absorption difference observed between said K line of said titanium and the 3.69 keV K line of calcium primarily in determining the $CaCO_3$ content, and using the information provided by the attenuation of said calcium K line primarily for determining the combined content of talc and kaolin.

10. A method as claimed in claim 1, further comprising the step of measuring the attenuation in the object under measurement by beta radiation emitted by an $^{85}$Kr source to determine the base weight in g/m² of said paper.

11. A method as claimed in claim 1, wherein said measurements are carried out at at least two different angles of incidence ($\alpha$) of said radiation.

12. A method as claimed in claim 11, wherein said measurements are carried out at at least two different angles of departure ($\beta$) of the characteristic X-ray radiation excited in the specimen by said radiation.

13. A method as claimed in claim 12, wherein the angle of incidence ($\alpha$) of said radiation is equal in magnitude to the angle of departure ($\beta$) of the excited radiation relative to the plane of said paper or cardboard on the same side of the same.

14. Apparatus for measuring the distribution in the thickness direction of filler and/or coating materials of paper or cardboard, and the content of said materials, without destroying the specimen, said apparatus having a radio-isotope source providing radiation used to excite the characteristic X-ray radiation of the material component under examination, of the object of measurement, means for observing the intensity of said characteristic X-ray radiation, means for performing measurements on both sides of the paper or cardboard and for determining the contents of filler components by X-ray absorption measurements for eliminating the effects of these components disturbing the distribution measurement, and means for measuring the base weight, of the paper or cardboard under examination by radiation absorption measurement, said apparatus comprising
    a measuring unit having a power source, an amplifier, a counter, a processor and a display unit; and
    a measuring head connected to said measuring unit, said measuring head having radiation sources, transfer means for said radiation sources, a radiation transforming plate, transfer means for said plate, a radiation detector and a preamplifier connected to each other in a manner such as to perform absorption measurements for the determination of the contents of different filler components by utilizing radiation excited from different radiation sources.

15. Apparatus as claimed in claim 14, wherein said measuring unit further comprises a control unit which controls the measuring cycle and the processing of measurement results.

16. Apparatus as claimed in claim 14, wherein said radiation detector in said measuring head comprises a proportional counter.

17. Apparatus as claimed in claim 14, wherein said radiation detector in said measuring head comprises a semiconductor counter.

18. Apparatus as claimed in claim 14, further comprising a computer connected to said measuring unit, said computer being programmed with a measurement result-processing and outputting program.

19. Apparatus as claimed in claim 14 wherein said measuring head is disposed to traverse reciprocatingly over the entire width of the specimen or part thereof.

* * * * *